United States Patent
Overmyer et al.

(10) Patent No.: US 11,559,366 B2
(45) Date of Patent: Jan. 24, 2023

(54) COMMUNICATING CLOSURE EFFORT FOR ROBOTIC SURGICAL TOOLS BACKGROUND

(71) Applicant: Ethicon LLC, Guaynabo, PR (US)

(72) Inventors: Mark D. Overmyer, Cincinnati, OH (US); Sol A. Posada, Landsdale, PA (US); Kris Eren Kallenberger, Cincinnati, OH (US); Christopher A. Denzinger, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 672 days.

(21) Appl. No.: 16/587,744

(22) Filed: Sep. 30, 2019

(65) Prior Publication Data

US 2021/0093409 A1    Apr. 1, 2021

(51) Int. Cl.
| | |
|---|---|
| *A61B 34/00* | (2016.01) |
| *A61B 34/35* | (2016.01) |
| *B25J 13/08* | (2006.01) |
| *B25J 19/06* | (2006.01) |
| *A61B 34/30* | (2016.01) |

(52) U.S. Cl.
CPC .............. *A61B 34/74* (2016.02); *A61B 34/35* (2016.02); *B25J 13/085* (2013.01); *B25J 13/088* (2013.01); *B25J 19/061* (2013.01); *A61B 2034/305* (2016.02)

(58) Field of Classification Search
CPC ... A61B 34/74; A61B 34/35; A61B 2034/305; A61B 34/76; A61B 34/37; A61B 34/30; B25J 13/085; B25J 13/088; B25J 19/061

USPC ..... 700/245–264; 318/568.11–568.25; 606/1
See application file for complete search history.

(56) References Cited

U.S. PATENT DOCUMENTS

| | | | | |
|---|---|---|---|---|
| 5,417,210 A | * | 5/1995 | Funda | B25J 9/04 600/109 |
| 6,988,295 B2 | * | 1/2006 | Tillim | A61B 17/2909 16/110.1 |
| 7,506,409 B2 | * | 3/2009 | Tillim | B60T 7/08 16/110.1 |

(Continued)

FOREIGN PATENT DOCUMENTS

EP    3431025 A1    1/2019

OTHER PUBLICATIONS

ISR—WO from application PCT/IB2020/058830 dated Dec. 7, 2020 and that claims priority to the present US application.

*Primary Examiner* — Jaime Figueroa
(74) *Attorney, Agent, or Firm* — Vorys, Sater, Seymour and Pease LLP (57) ABSTRACT

A method includes grasping a user input device in communication with a surgical tool of a robotic surgical system, the surgical tool including an end effector with opposing jaws, squeezing the user input device and thereby actuating a motor that closes the jaws and clamps down on tissue at a surgical site, and calculating with a computer system in communication with the surgical tool work completed by the motor to close the jaws and clamp down on the tissue. The computer system generates one or more effort indicators when the work completed by the motor meets or exceeds one or more predetermined work increments corresponding to operation of the motor, and communicates the one or more effort indicators to an operator.

20 Claims, 6 Drawing Sheets

(56) References Cited

U.S. PATENT DOCUMENTS

| | | | | | |
|---|---|---|---|---|---|
| 8,100,133 | B2* | 1/2012 | Mintz | | A61B 34/30 |
| | | | | | 606/1 |
| 8,256,323 | B2* | 9/2012 | Vellutini | | B62K 23/06 |
| | | | | | 74/502.2 |
| 8,418,073 | B2* | 4/2013 | Mohr | | A61B 18/12 |
| | | | | | 715/764 |
| 8,734,312 | B2* | 5/2014 | Conner | | A61B 34/37 |
| | | | | | 600/130 |
| 8,831,782 | B2* | 9/2014 | Itkowitz | | A61B 34/76 |
| | | | | | 606/1 |
| 9,527,207 | B2* | 12/2016 | Low | | B25J 13/025 |
| 10,507,493 | B2* | 12/2019 | Houston | | H02K 7/061 |
| 10,610,303 | B2* | 4/2020 | Johnson | | G09B 23/285 |
| 10,768,708 | B1* | 9/2020 | Sills | | B25J 13/00 |
| 11,013,559 | B2* | 5/2021 | Johnson | | G06F 3/0346 |
| 11,270,601 | B2* | 3/2022 | Yu | | G06F 3/014 |
| 2003/0074766 | A1* | 4/2003 | Tillim | | B25G 1/102 |
| | | | | | 16/430 |
| 2007/0270685 | A1* | 11/2007 | Kang | | A61B 34/76 |
| | | | | | 600/424 |
| 2010/0228249 | A1* | 9/2010 | Mohr | | A61B 34/37 |
| | | | | | 715/764 |
| 2010/0313696 | A1* | 12/2010 | Vellutini | | B62K 23/06 |
| | | | | | 74/491 |
| 2011/0077663 | A1* | 3/2011 | Sundaresan | | A61B 17/320725 |
| | | | | | 606/130 |
| 2011/0152881 | A1* | 6/2011 | Conner | | A61B 34/76 |
| | | | | | 606/130 |
| 2011/0295242 | A1* | 12/2011 | Spivey | | A61B 17/068 |
| | | | | | 606/1 |
| 2012/0272783 | A1* | 11/2012 | Vellutini | | B62K 23/06 |
| | | | | | 74/523 |
| 2013/0066304 | A1* | 3/2013 | Belson | | A61B 1/3132 |
| | | | | | 606/1 |
| 2014/0031983 | A1* | 1/2014 | Low | | B25J 9/0087 |
| | | | | | 700/259 |
| 2014/0180477 | A1 | 6/2014 | Chung | | |
| 2018/0078319 | A1* | 3/2018 | Nobles | | A47B 21/02 |
| 2019/0133689 | A1* | 5/2019 | Johnson | | G06F 3/0346 |
| 2019/0201137 | A1 | 7/2019 | Shelton, IV | | |
| 2019/0247888 | A1* | 8/2019 | Houston | | H02K 33/00 |
| 2020/0205910 | A1* | 7/2020 | Jardine | | A61B 34/30 |
| 2020/0253677 | A1* | 8/2020 | Jinno | | A61B 34/32 |
| 2020/0352663 | A1* | 11/2020 | Klingbeil | | G16H 40/67 |
| 2020/0356173 | A1* | 11/2020 | Bajaj | | H02P 25/064 |
| 2021/0030495 | A1* | 2/2021 | Savall | | A61B 34/76 |

* cited by examiner

COMMUNICATING CLOSURE EFFORT FOR ROBOTIC SURGICAL TOOLS

BACKGROUND

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy in which one or more small incisions are formed in the abdomen of a patient and a trocar is inserted through the incision to form a pathway that provides access to the abdominal cavity. The trocar is used to introduce various instruments and tools into the abdominal cavity, as well as to provide insufflation to inflate and thereby elevate the abdominal wall above the organs. The instruments can be used to engage and/or treat tissue in a number of ways to achieve a diagnostic or therapeutic effect.

Each surgical tool typically includes an end effector arranged at its distal end. Example end effectors include clamps, graspers, scissors, staplers, and needle holders, and are similar to those used in conventional (open) surgery except that the end effector of each tool is separated from its handle by an approximately 12-inch long shaft. A camera or image capture device, such as an endoscope, is also commonly introduced into the abdominal cavity to enable the surgeon to view the surgical field and the operation of the end effectors during operation. The surgeon is able to view the procedure in real-time by means of a visual display in communication with the image capture device.

Surgical staplers are one type of end effector capable of cutting and simultaneously stapling (fastening) transected tissue. Sometimes referred to as an "endocutter," the surgical stapler includes opposing jaws capable of opening and closing to grasp and release tissue. Once tissue is grasped or clamped between the opposing jaws, the end effector may be "fired" to advance a cutting element or knife distally to transect the grasped tissue. As the cutting element advances, staples contained within the end effector are progressively deployed to seal opposing sides of the transected tissue.

Technological advances have allowed surgical tools, such as surgical staplers, to be used in robotic surgical systems. In robotic surgery, a surgical tool is mounted to a robotic arm of a robotic manipulator, and a surgeon is able to remotely operate the surgical tool from a master control console in communication with the robotic manipulator. The master control console includes one or more user input devices that can be grasped by the surgeon (e.g., one in each hand) and physically manipulated in space to cause the corresponding surgical tools to move, articulate, and actuate as the surgeon desires.

One drawback to operating surgical tools via a robotic system, however, is the general loss of tactile feedback that manually operated surgical tools provide to the surgeon during operation. With robotic surgical systems, the surgeon cannot directly feel the physical force required to grasp onto tissue, which can be a useful metric in confirming tissue thickness and staple sizes, for example. What is needed is a way to provide feedback to the surgeon operating a robotic surgical instrument of the effort the robot used to grasp tissue.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgical systems and, more particularly, to systems and methods of calculating the work used to grasp a robotic surgical tool on tissue and communicating the grasping work to the user for consideration. One example method includes grasping a user input device in communication with a surgical tool of a robotic surgical system, the surgical tool including an end effector with opposing jaws. The user input device may then be squeezed, which causes a motor to actuate and thereby close the jaws and clamp down on tissue at a surgical site. A computer system may be programmed or otherwise configured to calculate work completed by the motor to close the jaws and clamp down on the tissue, and may be further programmed to generate one or more effort indicators when the work completed by the motor meets or exceeds one or more predetermined work increments corresponding to operation of the motor. The effort indicators may be provided to the operator using any form of sensory feedback, such as auditory feedback, tactile feedback, visual feedback, or any combination thereof. As will be appreciated, this may provide the operator with a consistent and reliable replacement for the tactile feedback common to manually operated surgical tools but absent in robotic surgical tools.

Figure 1:
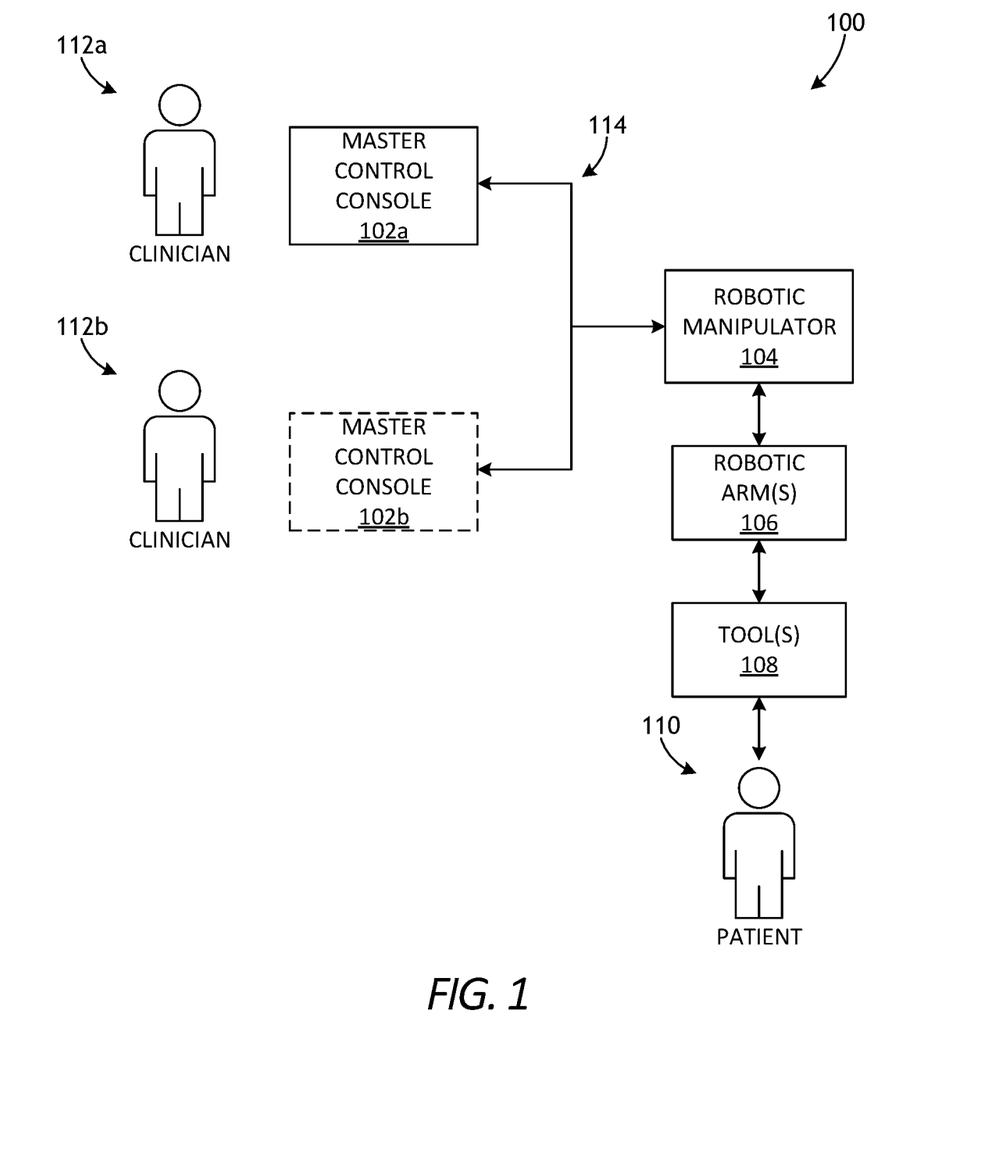
FIG. 1 is a block diagram of an example robotic surgical system that may incorporate some or all of the principles of the present disclosure.
Figure 2:
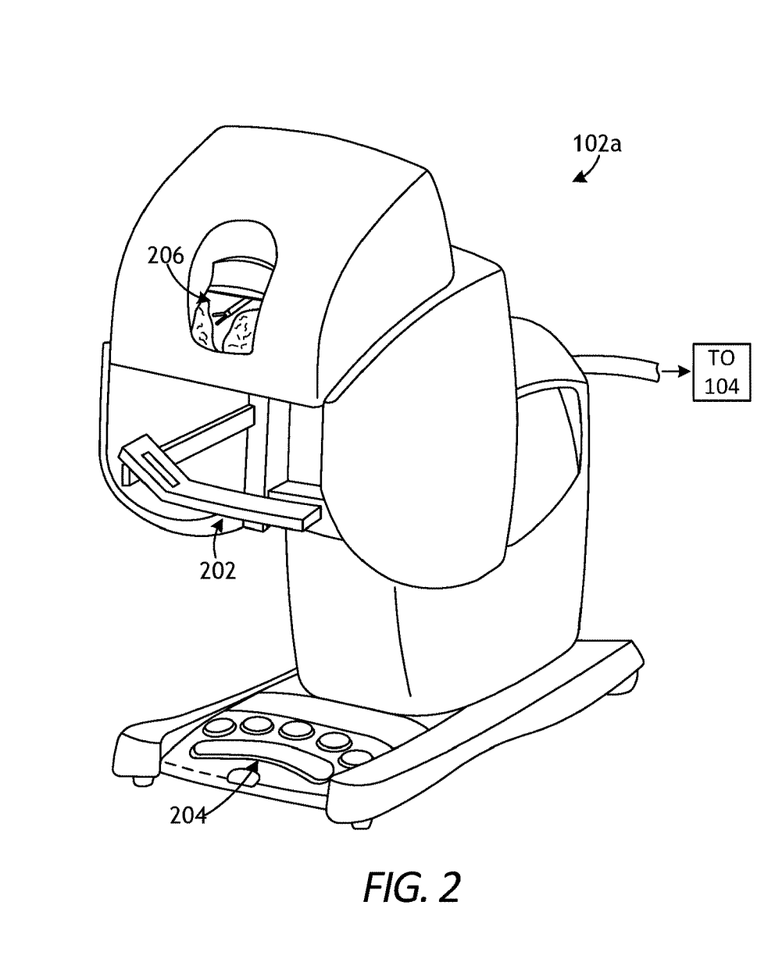
FIG. 2 is an example embodiment of one of the master control consoles of FIG. 1.
Figure 3:
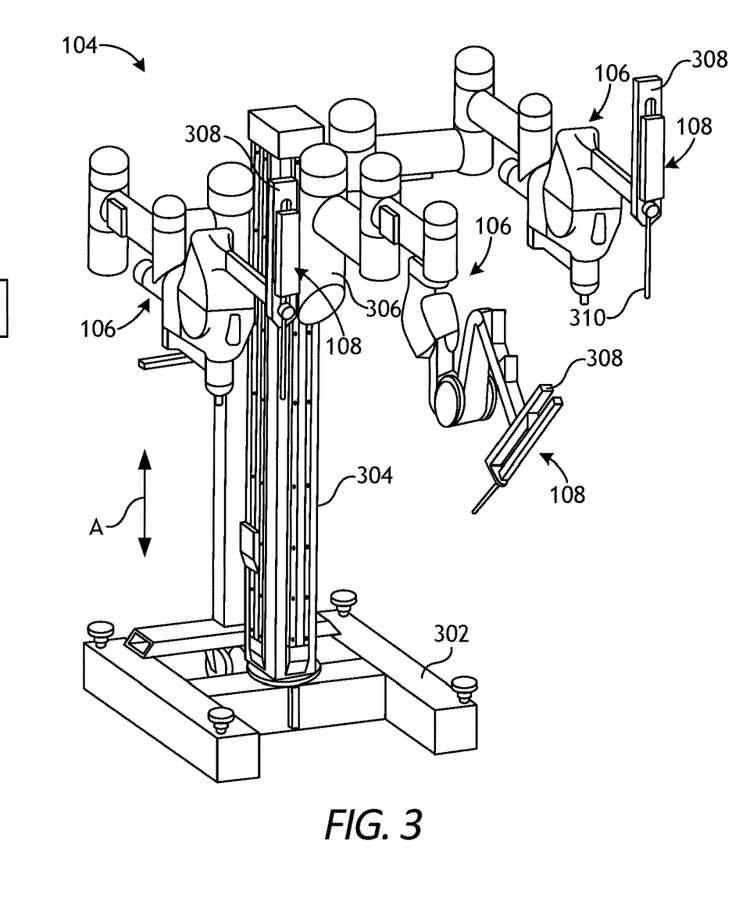
FIG. 3 depicts one example of the robotic manipulator of FIG. 1, according to one or more embodiments.

FIGS. 1-3 illustrate the structure and operation of an example robotic surgical system and associated components thereof. While applicable to robotic surgical systems, it is noted that the principles of the present disclosure may alternatively be applied to non-robotic surgical systems, without departing from the scope of the disclosure.

FIG. 1 is a block diagram of an example robotic surgical system 100 that may incorporate some or all of the principles of the present disclosure. As illustrated, the system 100 can include at least one master control console 102*a* and at least one robotic manipulator 104. The robotic manipulator 104 may be mechanically and/or electrically coupled to or otherwise include one or more robotic arms 106. In some embodiments, the robotic manipulator 104 may be mounted to a transport cart (alternately referred to as an "arm cart") that enables mobility of the robotic manipulator 104 and the associated robotic arms 106. Each robotic arm 106 may include and otherwise provide a tool driver where one or more surgical instruments or tools 108 may be mounted for performing various surgical tasks on a patient 110. Operation of the robotic arms 106, the corresponding tool drivers, and the associated tools 108 may be directed by a clinician 112a (e.g., a surgeon) from the master control console 102a.

In some embodiments, a second master control console 102b (shown in dashed lines) operated by a second clinician 112b may also help direct operation of the robotic arms 106 and the tools 108 in conjunction with the first clinician 112a. In such embodiments, for example, each clinician 112a,b may control different robotic arms 106 or, in some cases, complete control of the robotic arms 106 may be passed between the clinicians 112a,b. In some embodiments, additional robotic manipulators having additional robotic arms may be utilized during surgery on a patient 110, and these additional robotic arms may be controlled by one or more of the master control consoles 102a,b.

The robotic manipulator 104 and the master control consoles 102a,b may communicate with one another via a communications link 114, which may be any type of wired or wireless communications link configured to carry suitable types of signals (e.g., electrical, optical, infrared, etc.) according to any communications protocol. The communications link 114 may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network. Accordingly, the clinicians 112a,b may be able to remotely control operation of the robotic arms 106 via the communications link 114, thus enabling the clinicians 112a,b to operate on the patient 110 remotely.

FIG. 2 is one example embodiment of the master control console 102a that may be used to control operation of the robotic manipulator 104 of FIG. 1. As illustrated, the master control console 102a can include a support 202 on which the clinician 112a,b (FIG. 1) can rest his/her forearms while gripping two user input devices (not shown), one in each hand. The user input devices can comprise, for example, physical controllers such as, but not limited to, hand-held actuator modules, a joystick, exoskeletal gloves, a master manipulator, etc., and may be movable in multiple degrees of freedom to control the position and operation of the surgical tool(s) 108 (FIG. 1). The master control console 102a may further include one or more foot pedals 204 engageable by the clinician 112a,b to change the configuration of the surgical system and/or generate additional control signals to control operation of the surgical tool(s) 108.

The user input devices and/or the foot pedals 204 may be manipulated while the clinician 112a,b (FIG. 1) views the procedure via a visual display 206. Images displayed on the visual display 206 may be obtained from an endoscopic camera or "endoscope." In some embodiments, as described in more detail below, the visual display 206 may include or otherwise incorporate a force feedback meter or "effort indicator" that provides the clinician 112a,b with a visual indication of the magnitude of force being assumed by the surgical tool (i.e., a cutting instrument or dynamic clamping member) and in which direction. As will be appreciated, other sensor arrangements may be employed to provide the master control console 102a with an indication of other surgical tool metrics, such as whether a staple cartridge has been loaded into an end effector or whether an anvil has been moved to a closed position prior to firing, for example.

FIG. 3 depicts one example of the robotic manipulator 104 that may be used to operate a plurality of surgical tools 108, according to one or more embodiments. As illustrated, the robotic manipulator 104 may include a base 302 that supports a vertically extending column 304. A plurality of robotic arms 106 (three shown) may be operatively coupled to the column 304 at a carriage 306 that can be selectively adjusted to vary the height of the robotic arms 106 relative to the base 302, as indicated by the arrow A.

The robotic arms 106 may comprise manually articulable linkages, alternately referred to as "set-up joints." In the illustrated embodiment, a surgical tool 108 is mounted to corresponding tool drivers 308 provided on each robotic arm 106. Each tool driver 308 may include one or more drivers or motors used to interact with a corresponding one or more drive inputs of the surgical tools 108, and actuation of the drive inputs causes the associated surgical tool 108 to operate.

One of the surgical tools 108 may comprise an image capture device 310, such as an endoscope, which may include, for example, a laparoscope, an arthroscope, a hysteroscope, or may alternatively include some other imaging modality, such as ultrasound, infrared, fluoroscopy, magnetic resonance imaging, or the like. The image capture device 310 has a viewing end located at the distal end of an elongate shaft, which permits the viewing end to be inserted through an entry port into an internal surgical site of a patient's body. The image capture device 310 may be communicably coupled to the visual display 206 (FIG. 2) and capable of transmitting images in real-time to be displayed on the visual display 206.

The remaining surgical tools may be communicably coupled to the user input devices held by the clinician 112a,b (FIG. 1) at the master control console 102a (FIG. 2). Movement of the robotic arms 106 and associated surgical tools 108 may be controlled by the clinician 112a,b by manipulating the user input device(s). Each surgical tool 108 may include or otherwise incorporate an end effector mounted on a corresponding articulable wrist pivotally mounted on a distal end of an associated elongate shaft. The elongate shaft permits the end effector to be inserted through entry ports into the internal surgical site of a patient's body. Operation (actuation) of the end effector may also be controlled by the clinician 112a,b by manipulating the user input device(s).

In use, the robotic manipulator 104 is positioned close to a patient requiring surgery and normally caused to remain stationary until a surgical procedure to be performed has been completed. The robotic manipulator 104 typically has wheels or casters to render it mobile. The lateral and vertical positioning of the robotic arms 106 may be set by the clinician 112a,b (FIG. 1) to facilitate passing the elongate shafts of the surgical tools 108 and the image capture device 310 through the entry ports to desired positions relative to the surgical site. When the surgical tools 108 and image capture device 310 are so positioned, the robotic arms 106 and carriage 306 can be locked in position.

Figures 4, 5:
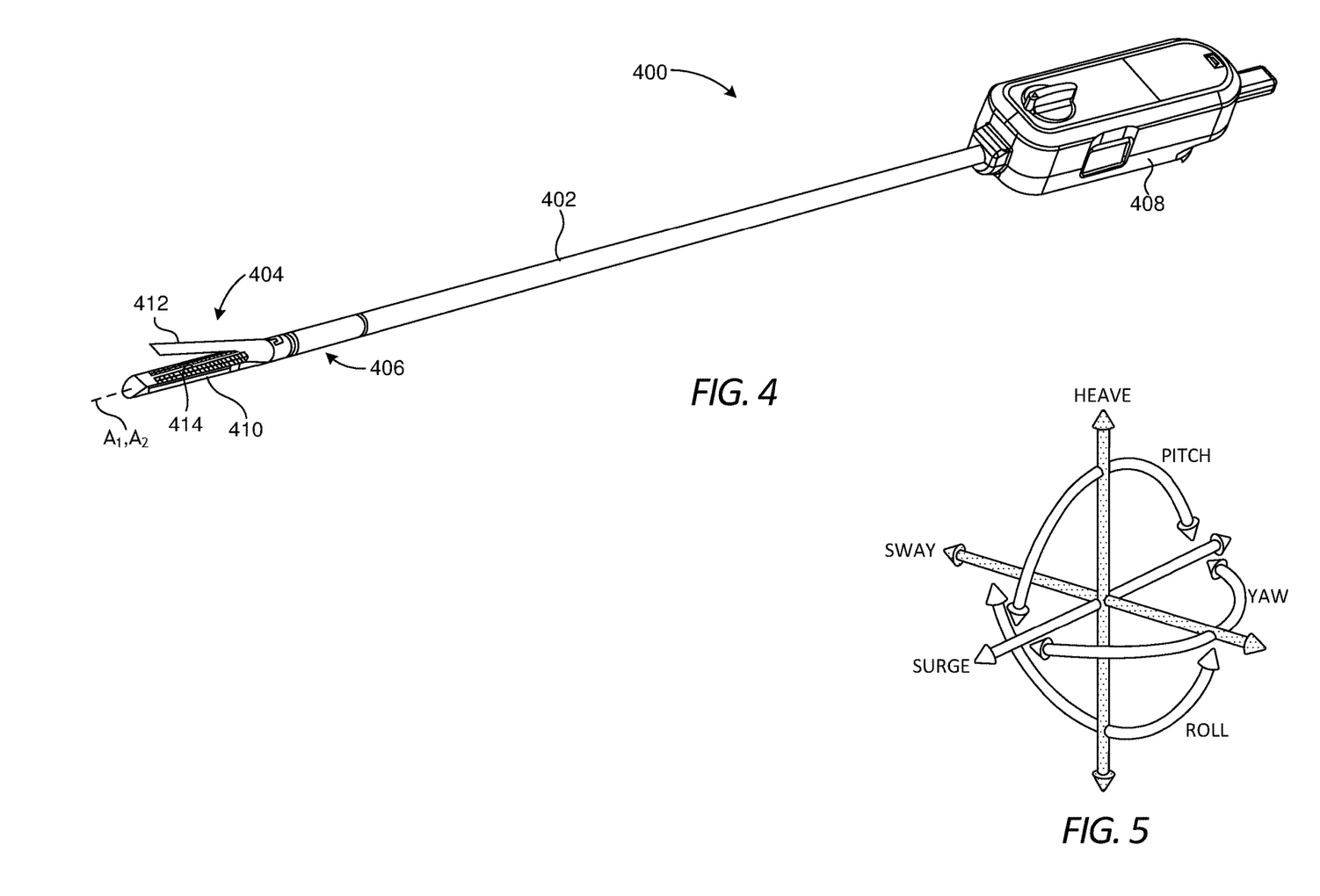
FIG. 4 is an isometric side view of an example surgical tool that may incorporate some or all of the principles of the present disclosure.
FIG. 5 illustrates potential degrees of freedom in which the wrist of FIG. 4 may be able to articulate (pivot).

FIG. 4 is an isometric side view of an example surgical tool 400 that may incorporate some or all of the principles of the present disclosure. The surgical tool 400 may be the same as or similar to at least one of the surgical tools 108 of FIGS. 1 and 3 and, therefore, may be used in conjunction with a robotic surgical system, such as the robotic surgical system 100 of FIG. 1. As illustrated, the surgical tool 400 includes an elongated shaft 402, an end effector 404, an articulable wrist 406 (alternately referred to as a "wrist joint") that couples the end effector 404 to the distal end of the shaft 402, and a drive housing 408 coupled to the proximal end of the shaft 402. In applications where the surgical tool 400 is used in conjunction with a robotic surgical system, the drive housing 408 can include coupling features that releasably couple the surgical tool 400 to the robotic surgical system. The principles of the present disclosure, however, are equally applicable to surgical tools that are non-robotic and otherwise capable of manual manipulation.

The terms "proximal" and "distal" are defined herein relative to a robotic surgical system having an interface configured to mechanically and electrically couple the surgical tool 400 (e.g., the drive housing 408) to a robotic manipulator. The term "proximal" refers to the position of an element closer to the robotic manipulator and the term "distal" refers to the position of an element closer to the end effector 404 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 400 can have any of a variety of configurations capable of performing one or more surgical functions. In the illustrated embodiment, the end effector 404 comprises a surgical stapler, alternately referred to as an "Endocutter," configured to simultaneously cut and staple (fasten) tissue. As illustrated, the end effector 404 includes opposing jaws 410, 412 configured to move (articulate) between open and closed positions. The opposing jaws 410, 412, however, may alternately form part of other types of end effectors that include jaws such as, but not limited to, tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), etc. One or both of the jaws 410, 412 may be configured to pivot to actuate the end effector 404 between the open and closed positions. In the illustrated example, the second jaw 412 is rotatable (pivotable) relative to the first jaw 410 to move between an open, unclamped position and a closed, clamped position. In other embodiments, however, the first jaw 410 may move (rotate) relative to the second jaw 412, without departing from the scope of the disclosure.

In the illustrated example, the first jaw 410 may be characterized or otherwise referred to as a "cartridge" jaw, and the second jaw 412 may be characterized or otherwise referred to as an "anvil" jaw. More specifically, the first jaw 410 may include a frame that houses or supports a staple cartridge that contains staples, and the second jaw 412 is pivotally supported relative to the first jaw 410 and defines a surface that operates as an anvil to deform staples ejected from the staple cartridge during operation.

The wrist 406 enables the end effector 404 to articulate (pivot) relative to the shaft 402 and thereby position the end effector 404 at desired orientations and locations relative to a surgical site. FIG. 5 illustrates the potential degrees of freedom in which the wrist 406 may be able to articulate (pivot). The wrist 406 can have any of a variety of configurations. In general, the wrist 406 comprises a joint configured to allow pivoting movement of the end effector 404 relative to the shaft 402. The degrees of freedom of the wrist 406 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 404) with respect to a given reference Cartesian frame. As depicted in FIG. 5, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 406 (e.g., X-axis), yaw movement about a second axis of the wrist 406 (e.g., Y-axis), and combinations thereof to allow for 360° rotational movement of the end effector 404 about the wrist 406. In other applications, the pivoting motion can be limited to movement in a single plane, e.g., only pitch movement about the first axis of the wrist 406 or only yaw movement about the second axis of the wrist 406, such that the end effector 404 moves only in a single plane.

Referring again to FIG. 4, the surgical tool 400 may incorporate or include an actuation system designed to facilitate articulation of the wrist 406 and actuation (operation) of the end effector 404 (e.g., clamping, firing, rotation, articulation, energy delivery, etc.). The actuation system may include a plurality of drive members or the like (obscured in FIG. 4) that extend from the drive housing 408 to the wrist 406, and selective actuation of these drive members causes the end effector 404 to articulate (pivot) relative to the shaft 402 at the wrist 406. The end effector 404 is depicted in FIG. 4 in the unarticulated position where a longitudinal axis $A_2$ of the end effector 404 is substantially aligned with the longitudinal axis $A_1$ of the shaft 402, such that the end effector 404 is at a substantially zero angle relative to the shaft 402. In the articulated position, the longitudinal axes $A_1$, $A_2$ would be angularly offset from each other such that the end effector 404 is at a non-zero angle relative to the shaft 402.

Other drive members may extend to the end effector 404, and selective actuation of those drive members may cause the end effector 404 to actuate (operate). Actuating the end effector 404 may include closing and/or opening the second jaw 412 relative to the first jaw 410 (or vice versa), thereby enabling the end effector 404 to grasp (clamp) onto tissue. Once tissue is grasped or clamped between the opposing jaws 410, 412, actuating the end effector 404 may further include "firing" the end effector 404, which may refer to causing a cutting element or knife (not visible) to advance distally within a slot 414 defined in the second jaw 410. As it moves distally, the cutting element may transect any tissue grasped between the opposing jaws 410, 412. Moreover, as the cutting element advances distally, a plurality of staples contained within the staple cartridge (e.g., housed within the first jaw 410) may be urged (cammed) into deforming contact with corresponding anvil surfaces (e.g., pockets) provided on the second jaw 412. The deployed staples may form multiple rows of staples that seal opposing sides of the transected tissue.

In some applications, the surgical tool 400 may also be configured to apply energy to tissue, such as radio frequency (RF) energy. In such cases, actuating the end effector 404 may further include applying energy to tissue grasped or clamped between two opposing jaws to cauterize or seal the captured tissue, following which the tissue may be transected.

Figure 6:
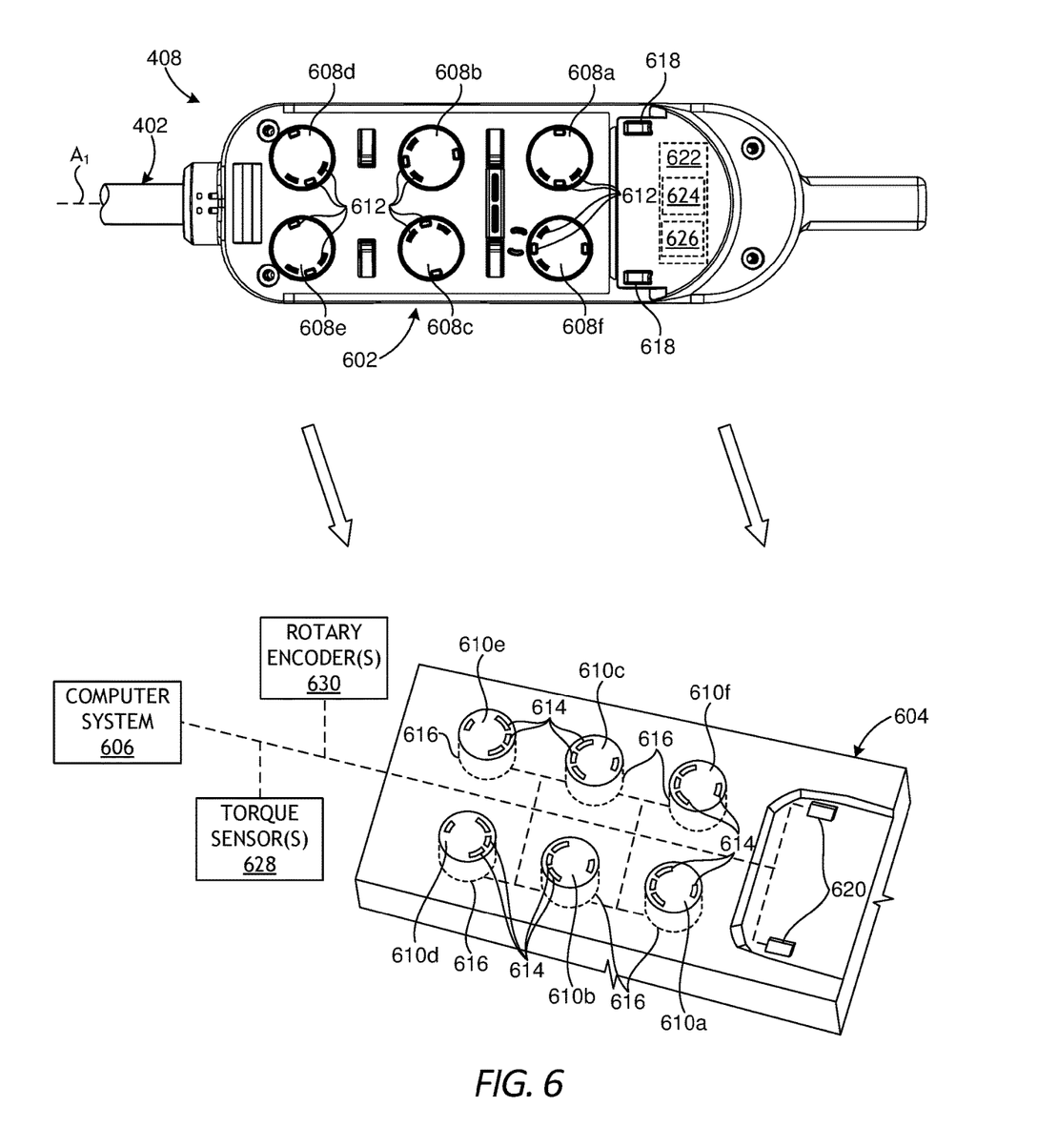
FIG. 6 is a bottom view of the drive housing of FIG. 4, according to one or more embodiments.

FIG. 6 is a bottom view of the drive housing 408, according to one or more embodiments. As illustrated, the drive housing 408 may include a tool mounting portion 602 used to operatively couple the drive housing 408 to a tool driver 604. The tool driver 604 may be the same as or similar to the tool drivers 308 of FIG. 3, and may thus be operable in conjunction with the robotic manipulator 104 of FIGS. 1 and 3. Mounting the drive housing 408 to the tool driver 604 places the drive housing 408 in communication with a computer system 606, which may communicate with or otherwise form part of the master controllers 102a,b (FIG. 1). The computer system 608 monitors and directs operation of the drive housing 408 via operation of the tool driver 604, thus enabling a user (e.g., the clinicians 112a,b of FIG. 1) to control operation of the drive housing 408 by working through the master controller 102a,b.

The tool mounting portion 602 includes and otherwise provides an interface that mechanically, magnetically, and/or electrically couples the drive housing 408 to the tool driver 604. In at least one embodiment, the tool mounting portion 602 couples the drive housing 408 to the tool driver 604 via a sterile barrier (not shown). As illustrated, the interface can include and support a plurality of drive inputs, shown as drive inputs 608a, 608b, 608c, 608d, 608e, and 608f. Each drive input 608a-f may comprise a rotatable disc configured to align and mate with a corresponding driver 610a, 610b, 610c, 610d, 610e, and 610f of the tool driver 604. Each drive input 608a-f and corresponding driver 610a-f provide or define one or more matable surface features 612 and 614, respectively, configured to facilitate mating engagement between the opposing surface features 612, 614 such that movement (rotation) of a given driver 610a-f correspondingly moves (rotates) the associated drive input 608a-f.

Each driver 610a-f may include or otherwise comprise a motor 616 configured to actuate the corresponding driver 610a-f, and actuation of a given driver 610a-f correspondingly causes actuation of the mated drive input 608a-f, which facilitates operation of the internal mechanics of the drive housing 408. More specifically, actuation of the motors 616 may cause rotational movement of the corresponding driver 610a-f, which, in turn, rotates the associated drive input 608a-f. Each motor 616 may be in communication with the computer system 606 and, based on input signals provided by a user (e.g., a surgeon), the computer system 606 may selectively cause any of the motors 616 to actuate and thereby drive the corresponding driver 610a-f to operate the tool.

In some embodiments, actuation of the first drive input 608a via the first driver 610a may control rotation of the shaft 402 about its longitudinal axis $A_1$. Depending on the rotational direction of the first drive input 608a, the shaft 402 can be rotated clockwise or counter-clockwise, thus correspondingly rotating the end effector 404 (FIG. 4) in the same direction. Actuation of the second and third drive inputs 608b,c via the second and third drivers 610a,b, respectively, may control articulation of the end effector 404 at the wrist 406 (FIG. 4). Actuation of the fourth and fifth drive inputs 608d,e via the fourth and fifth drivers 610d,e, respectively, may cause an outer portion of the shaft 402 (referred to herein as a "closure tube") to advance and retract, which closes and opens the jaws 410, 412 (FIG. 4). Lastly, actuation of the sixth drive input 608f via the sixth driver 610f may cause the end effector 404 to fire, which may entail distal deployment of a cutting element to transect tissue grasped by the jaws 410, 412 and simultaneous deployment of staples contained within the staple cartridge housed within the first jaw 410.

The tool mounting portion 602 may further include one or more electrical connectors 618 (two shown) configured to mate with corresponding electrical connections 620 (two shown) provided by the tool driver 604 to facilitate communication between the drive housing 408 and the tool driver 604. Alternately, the drive housing 408 can wirelessly communicate with the tool driver 604, such as through a near field communication connection. The drive housing 408 may further house or otherwise include an internal computer 622 that may include a memory 624 and/or a microprocessor 626. The memory 624 may include one or more databases or libraries that store data relating to the drive housing 408 and, more particularly, to the surgical tool 400 (FIG. 4). In some embodiments, the memory 624 may include non-transitory, computer-readable media such as a read-only memory (ROM), which may be PROM, EPROM, EEPROM, or the like. Mating the drive housing 408 to the tool driver 604 places the internal computer 622 in communication with the computer system 606.

The computer system 606 may be programmed and otherwise configured to monitor operation of the surgical tool 400 (FIG. 4) using various sensors and/or electromechanical devices, collectively referred to herein as "monitoring devices." Each monitoring device may be designed to monitor one or more operational parameters of the surgical tool 400 and report measured operational parameters to the computer system 606 for processing. The computer system 606, for example, may be in communication with one or more torque sensors 628 and/or one or more rotary encoders 630, each of which may be characterized as a monitoring device designed to monitor operational parameters of the surgical tool 400. The torque sensors 628, for instance, may be configured to monitor torque, and the rotary encoders 630 may be configured to monitor motion (rotational or linear).

The torque sensors 628 and the rotary encoders 630 may be incorporated into the motors 616 of some or all of the drivers 610a-f, but could alternatively be operatively coupled to one or more of the drive inputs 608a-f. The torque sensors 628 may be configured to measure the real-time torque loading on the motors 616, which corresponds to the torque loading assumed by the drivers 610a-f and/or the drive inputs 608a-f. The rotary encoders 630 may measure the rotational motion or output of the motors 616, which corresponds to the rotational motion of the drivers 610a-f and/or the drive inputs 608a-f. Monitoring torque loading and rotational motion of the motors 616 may help determine if the surgical tool 400 is operating in accordance with the commands provided by the computer system 606.

According to embodiments of the present disclosure, based on measurements acquired by the torque sensors 628 and/or the rotary encoders 630, the computer system 606 may be programmed and otherwise configured to calculate the work or effort required used to grasp tissue with the jaws 410, 412 (FIG. 4) of the end effector 404 (FIG. 4). The computer system 606 may further be programmed and otherwise configured to communicate the amount of real-time grasping work (effort) completed to the operator (e.g., the surgeon) in the form of an effort indicator. The effort indicator may be provided to the operator using any form of sensory feedback, such as for example auditory feedback, tactile feedback, visual feedback, or any combination thereof. Providing real-time effort indicators may provide the operator with a consistent and reliable replacement for the tactile feedback common to manually operated surgical tools but absent in robotic surgical tools. By receiving the effort indicators in real-time, the operator can repeatedly grasp the tissue to get the general "feel" of potential target tissue based on the effort indicators provided by the computer system 606.

In some cases, the magnitude of the effort indicator (e.g., auditory or tactile feedback, or shape of a visual feedback) with respect to grasp motor indicator could indicate tissue properties. For example, a visual effort indicator profile of healthy tissue could rise sharply, then settle out to a final value. A visual effort indicator profile of diseased tissue could gradually rise to the same final value as the healthy tissue. The healthy and diseased tissue samples may comprise, for instance, samples of the same portion of an organ (from different patients), irradiated vs. non-irradiated tissue, scarred vs. unscarred tissue, etc. The resulting visual effort indicator profiles, in addition to the magnitude, could indicate tissue properties.

Figure 7A:
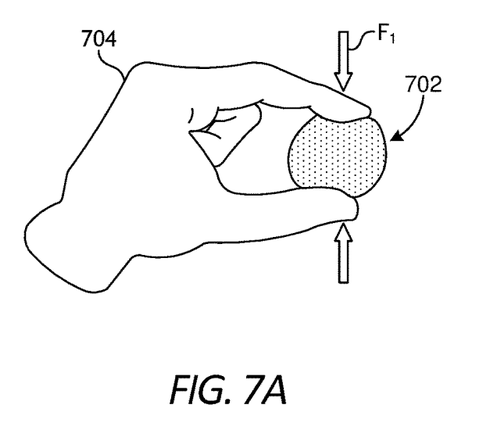
FIGS. 7A and 7B depict progressive operation of an example user input device, according to one or more embodiments.
Figure 7B:
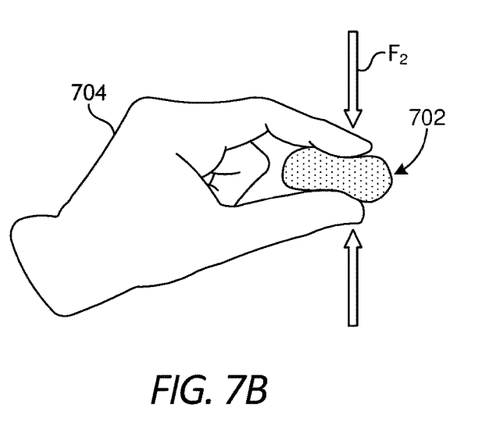

FIGS. 7A and 7B depict progressive operation of an example user input device 702, according to one or more embodiments, used to move, articulate, and/or actuate the surgical tool 400 (FIG. 4) and/or the end effector 404 (FIG. 4). As indicated above, example user input devices that may be used in a robotic surgical system can include hand-held actuator modules, a joystick, exoskeletal gloves, a master manipulator, or any combination thereof. In the illustrated embodiment, the user input device (UID) 702 comprises a type of hand-held actuator module that can be communicably coupled, either wired or wirelessly, to the master control console 102*a* (FIG. 2). Any physical manipulation of the UID 702 by the operator (e.g., surgeon) will be recognized by the master control console 102*a* and result in the movement, articulation, and/or actuation of the surgical tool 400 and/or the end effector 404.

As illustrated, the UID 702 can be grasped with the operator's hand 704, such as between the forefinger and the thumb of the hand 704. While grasped by the operator's hand 704, the UID 702 may be moved in multiple degrees of freedom to control the position of the end effector 404 (FIG. 4) relative to a surgical site. Moreover, the operator may be able to squeeze (compress) the UID 702 to cause actuation of the end effector 404, such as clamping with the jaws 410, 412 (FIG. 4). More specifically, squeezing the UID 702 between the forefinger and the thumb of the hand 704 (or any other portion of the hand 704) may generate corresponding signals sent to the computer system 606 (FIG. 6) to cause operation (e.g., rotation) of the fourth and fifth drivers 610*d,e* (FIG. 6), which drive the fourth and fifth drive inputs 608*d,e* (FIG. 6), respectively, to close and open the jaws 410, 412 (FIG. 4).

In at least one embodiment, the resulting closing and grasping force applied at the jaws 410, 412 by the robot will depend on how hard the operator squeezes the UID 702. In FIG. 7A, for example, the UID 702 is shown being squeezed between the forefinger and thumb of the hand 704 with a first force $F_1$, which equates to a proportional amount of force applied at the jaws 410, 412 (FIG. 4) by the robotic surgical system. In FIG. 7B, the UID 702 is squeezed with a second force $F_2$ that is greater than the first force $F_1$, which equates to a greater proportional amount of force applied at the jaws 410, 412 by the robotic surgical system.

Referring again to FIG. 6, in some embodiments, as the operator manipulates (squeezes) the UID 702 (FIG. 7), the torque sensors 628 and the rotary encoders 630 measure the torque and the rotational angle, respectively, of the motor(s) 616 operating the fourth and fifth drivers 610*d,e* in real-time, and report these measurements to the computer system 606 in real-time. Based on the torque and the rotational angle measurements provided by the torque sensors 628 and the rotary encoders 630, respectively, the computer system 606 may then be programmed and otherwise configured to calculate the work completed by the motor(s) 616 in closing the jaws 410, 412 (FIG. 4). One or more real-time effort indicators indicative of the amount of grasping work completed by the jaws 410, 1412 may then be generated and communicated to the operator (e.g., the surgeon).

Figure 8:
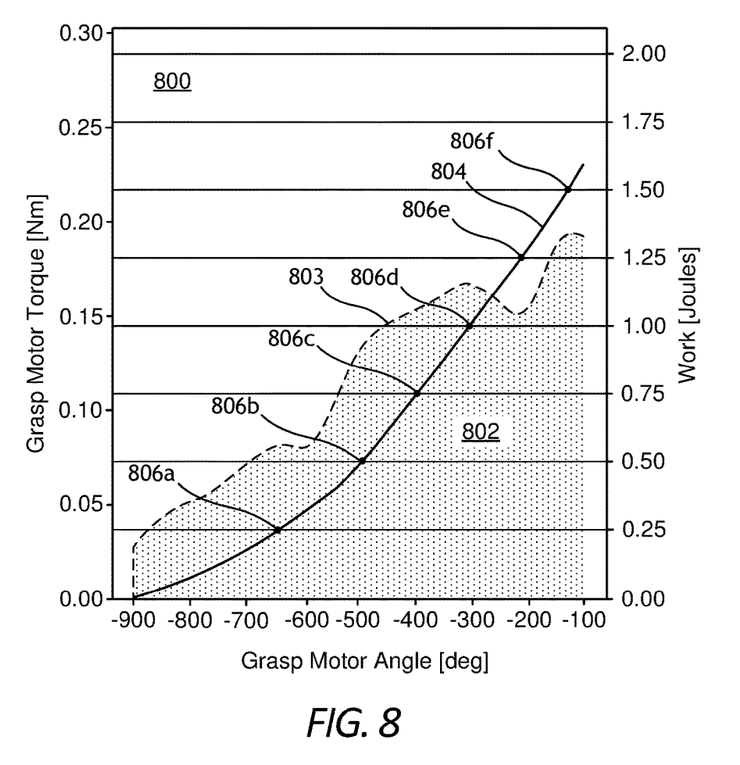
FIG. 8 is an example plot generated by the computer system of FIG. 6 based on torque and the rotational angle measurements.

FIG. 8 is an example plot 800 generated by the computer system 606 (FIG. 6) based on torque and rotational angle measurements obtained by the torque sensors 628 (FIG. 6) and the rotary encoders 630 (FIG. 6), respectively. More specifically, the plot 800 depicts an area 802 representative of the torque vs. the rotational angle measured on the motor(s) 616 (FIG. 6) while grasping the jaws 410, 412 (FIG. 4) on tissue. By taking the integral of an upper boundary 803 of the area 802, work 804 completed by the motor(s) 616 may be determined (calculated) and is represented on the plot 800 in the form of a line.

One or more predetermined work increments corresponding to operation of the motor(s) 616 (FIG. 6) may be set. If the measured work 804 meets or exceeds a predetermined work increment, the computer system 606 (FIG. 6) may then be programmed to communicate a corresponding effort indicator to the operator in real-time indicative of the amount of grasping work completed. In the illustrated embodiment, for example, predetermined work increments 806 comprise work increments of a set magnitude of 0.25 Joules, which are indicated on the plot 800 as predetermined work increments 806*a*, 806*b*, 806*c*, 806*d*, 806*e*, and 806*f*. As the work 804 completed by the motor(s) 616 meets or surpasses (exceeds) any of the predetermined work increments 806*a-f*, the computer system 606 (FIG. 6) may communicate a corresponding effort indicator to the operator in real-time to indicate that the amount of grasping work has met the particular predetermined work increment 806*a-f*. As will be appreciated, the work increments of the set magnitude can be any magnitude, without departing from the scope of the disclosure.

In some embodiments, the predetermined work increments 806*a-f* may alternatively comprise a percent of the total work possible for the motor(s) 616 (FIG. 6) to fully close the jaws 410, 412 (FIG. 4) and grasp onto tissue. For example, if grasping and fully closing the jaws 410, 412 requires 15 radians of angular movement for the motor(s) 616 and can use up to 0.5 Nm of torque, then the total possible work for the jaws 410, 412 to fully close and grasp onto tissue is 7.5 joules. In such embodiments, the predetermined work increments 806*a-f* could be set in increments of 5%, 10%, 15%, etc. of 7.5 joules, or any other desired multiple percentage. As the work 804 completed by the motor(s) 616 meets or surpasses (exceeds) any of the set percentages as predetermined work increments 806*a-f*, the computer system 606 (FIG. 6) may communicate a corresponding effort indicator to the operator.

In some embodiments, the work 804 may only increase in one angular direction of motor 616 (FIG. 6) travel. In such embodiments, travel of the motor 616 in the opposite angular direction may reset the calculation for the calculated work 804. As will be appreciated, resetting the calculation for the calculated work 804 upon reversal of the motor(s) 616 prevents combining the work calculated for a first grasp event with that of a second.

The effort indicators may be provided to the operator in the form of sensory feedback that can be recognized by at least one of the operator's senses. In some embodiments, for example, the effort indicator may comprise auditory (audible) feedback that can be heard by the operator. In such embodiments, an audible noise or sound may be generated as the work 804 completed by the motor(s) 616 (FIG. 6) meets or surpasses a predetermined work increment 806*a-f*. In one or more embodiments, the audible noise may comprise a brief sound, such as a tone or a "click" (collectively referred to herein as "a sound") that can be heard by the operator. In some embodiments, the pitch of the sound or tone may increase with each succeeding predetermined work increment 806*a-f* that is reached or surpassed during operation. Accordingly, in such embodiments, as the pitch of the sound increases, that is an indication to the operator that the closing force of the jaws 410, 412 (FIG. 4) is correspondingly increasing.

In other embodiments, the effort indicators may comprise tactile feedback that can be physically felt by the operator. In such embodiments, for example, the UID 702 (FIG. 7) may generate a brief vibration as the work 804 completed by the motor(s) 616 (FIG. 6) meets or surpasses a predetermined work increment 806*a-f*. In some embodiments, the magnitude (strength) or duration of the vibration may increase with each succeeding predetermined work increment 806*a-f* that is reached or surpassed. Accordingly, in such embodiments, as the strength or duration of the vibration felt in the UID 702 increases, that is an indication to the operator that the closing force of the jaws 410, 412 (FIG. 4) is correspondingly increasing. In some embodiments, the effort indicators may comprise a combination of audible and tactile feedback, such as a vibration and a click or sound being generated simultaneously and communicated to the operator.

In yet other embodiments, the effort indicators may comprise visual feedback that can be seen (viewed) by the operator. The visual feedback may be provided to the operator in a variety of ways. In one or more embodiments, for example, a graphic, animation, or other visual representation of the work 804 completed by the motor(s) 616 (FIG. 6) may be provided on the visual display 206 (FIG. 2) to visually indicate to the operator when the work 804 meets or surpasses a predetermined work increment 806*a-f*. The effort indicator feedback may be delivered in real-time and any visual feedback will not obscure the surgical field viewable by the operator on the visual display 206 (FIG. 2). In some embodiments, the effort indicators may comprise a combination of audible, tactile, and visual feedback, or any combination thereof.

In at least one embodiment, the visual feedback may take the form of an animation of a meter rendered as on overlay on the visual display 206 (FIG. 2). In such embodiments, the animated meter may comprise, for example, a torque meter with a graphical display similar to a tachometer. In other embodiments, the visualized meter may also graphically show the range of previous values of work 804 obtained for the end effector 404 (FIG. 4) during historic operation.

Figure 9:
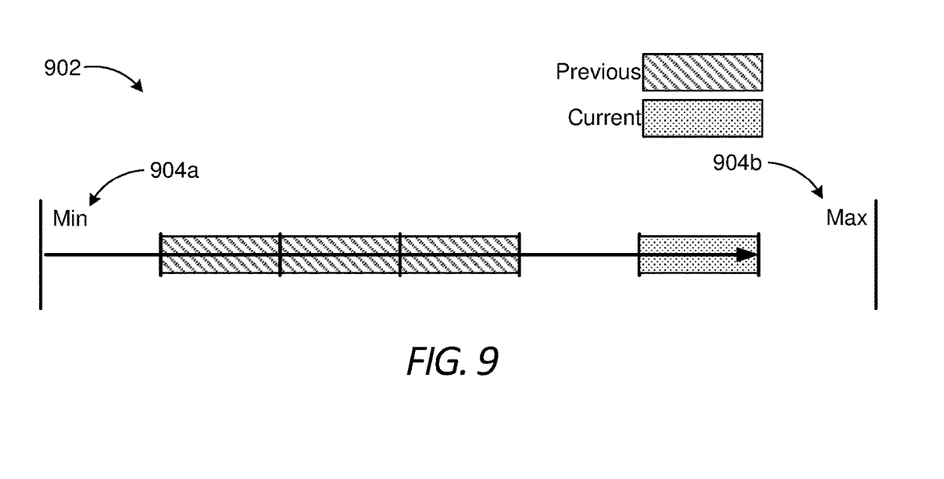
FIG. 9 depicts an example meter that may be graphically displayed for reference by the operator, according to one or more embodiments.

FIG. 9, for example, depicts an example meter 902 that may be graphically displayed for reference by the operator, according to one or more embodiments. The meter 902 may be rendered as on overlay on the visual display 206 (FIG. 2) and, as illustrated, graphically depicts the minimum 904*a* and the maximum 904*b* of the work 804 (FIG. 8) that can be completed by the motor(s) 616 (FIG. 6) in actuating the jaws 410, 412 (FIG. 4) of the end effector 402 (FIG. 4). In the illustrated embodiment, the meter 902 graphically depicts the range of previous values of work 804 obtained for the end effector 404 during historic operation thereof, in contrast to the current value of work 804 obtained for the end effector 404.

Graphically depicting the current and previous work 804 (FIG. 8) values may prove advantageous in helping the operator understand the type of tissue being grasped. For example, if the operator has already grasped on a given tissue several times, the work required to do so may be calculated and graphically displayed on the meter 902. Current grasping work is also graphically displayed in the meter 902 and, in the illustrated embodiment, is shown to be higher than previous attempts at grasping the tissue. This may be an indication that the tissue currently being grasped by the operator is thicker than the prior tissue grasped or that greater grasping force is required.

In some embodiments, the meter 902 may graphically display all historic values of work applicable to the end effector 404 (FIG. 4) and the jaws 410, 412 (FIG. 4) when grasping particular types of tissue (e.g., stomach tissue, intestine, lung, etc.). This historic data may be retrieved from a database, such as the memory 624 (FIG. 6) included in the internal computer 622 (FIG. 6) of the end effector 404, or may alternatively be retrieved from a cloud-based database that stores all historical measurements obtained during historic operation of the end effector 404.

Figure 10:
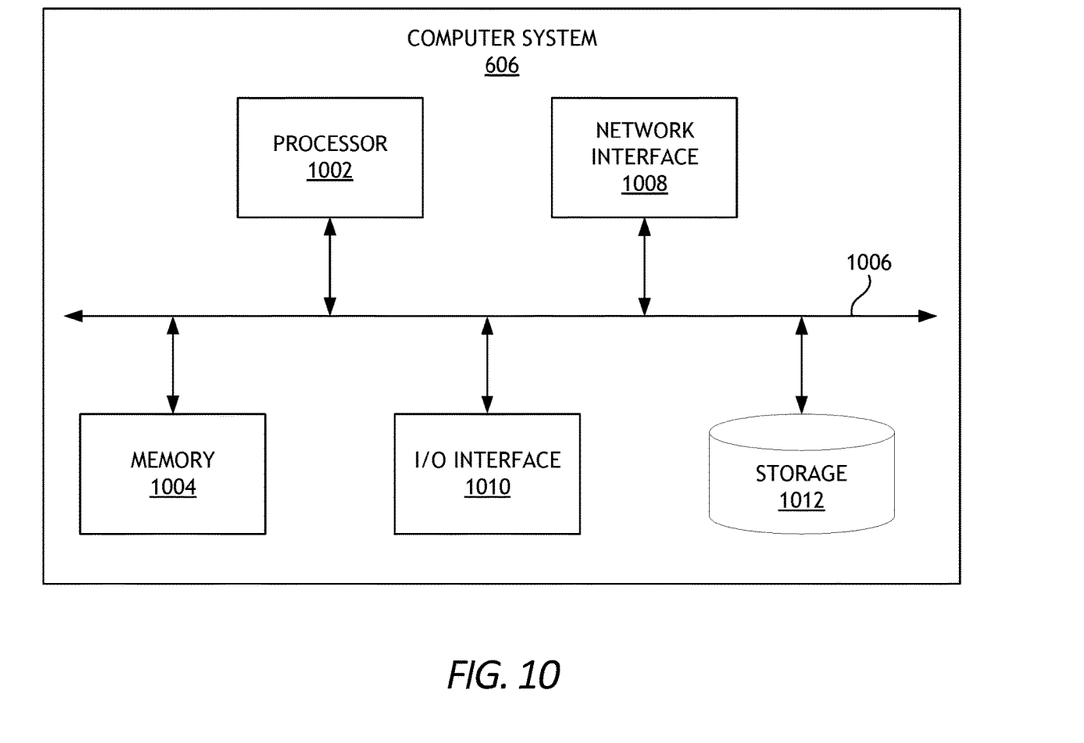
FIG. 10 illustrates an example embodiment of the computer system of FIG. 6.

FIG. 10 illustrates an example embodiment of the computer system 606 of FIG. 6. As shown, the computer system 606 includes one or more processors 1002, which can control the operation of the computer system 606. "Processors" are also referred to herein as "controllers." The processor(s) 1002 can include any type of microprocessor or central processing unit (CPU), including programmable general-purpose or special-purpose microprocessors and/or any one of a variety of proprietary or commercially available single or multi-processor systems. The computer system 606 can also include one or more memories 1004, which can provide temporary storage for code to be executed by the processor(s) 1002 or for data acquired from one or more users, storage devices, and/or databases. The memory 1004 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 606 can be coupled to a bus system 1006. The illustrated bus system 1006 is an abstraction that represents any one or more separate physical busses, communication lines/interfaces, and/or multi-drop or point-to-point connections, connected by appropriate bridges, adapters, and/or controllers. The computer system 606 can also include one or more network interface(s) 1008, one or more input/output (IO) interface(s) 1010, and one or more storage device(s) 1012.

The network interface(s) 1008 can enable the computer system 606 to communicate with remote devices, e.g., other computer systems, over a network, and can be, for non-limiting example, remote desktop connection interfaces, Ethernet adapters, and/or other local area network (LAN) adapters. The IO interface(s) 1010 can include one or more interface components to connect the computer system 606 with other electronic equipment. For non-limiting example, the IO interface(s) 1010 can include high-speed data ports, such as universal serial bus (USB) ports, 1394 ports, Wi-Fi, Bluetooth, etc. Additionally, the computer system 606 can be accessible to a human user, and thus the IO interface(s) 1010 can include displays, speakers, keyboards, pointing devices, and/or various other video, audio, or alphanumeric interfaces. The storage device(s) 1012 can include any conventional medium for storing data in a non-volatile and/or non-transient manner. The storage device(s) 1012 can thus hold data and/or instructions in a persistent state, i.e., the value(s) are retained despite interruption of power to the computer system 606. The storage device(s) 1012 can include one or more hard disk drives, flash drives, USB drives, optical drives, various media cards, diskettes, compact discs, and/or any combination thereof and can be directly connected to the computer system 606 or remotely connected thereto, such as over a network. In an exemplary embodiment, the storage device(s) 1012 can include a tangible or non-transitory computer readable medium configured to store data, e.g., a hard disk drive, a flash drive, a USB drive, an optical drive, a media card, a diskette, a compact disc, etc.

The elements illustrated in FIG. 10 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 606 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 606 can also include a web server for generating and/or delivering the web pages to client computer systems.

In an exemplary embodiment, the computer system 606 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

The computer system 606 can also include any of a variety of other software and/or hardware components, including by way of non-limiting example, operating systems and database management systems. Although an exemplary computer system is depicted and described herein, it will be appreciated that this is for the sake of generality and convenience. In other embodiments, the computer system may differ in architecture and operation from that shown and described here.

Embodiments disclosed herein include:

A. A method that includes grasping a user input device in communication with a surgical tool of a robotic surgical system, the surgical tool including an end effector with opposing jaws, squeezing the user input device and thereby actuating a motor that closes the jaws and clamps down on tissue at a surgical site, calculating with a computer system in communication with the surgical tool work completed by the motor to close the jaws and clamp down on the tissue, generating with the computer system one or more effort indicators when the work completed by the motor meets or exceeds one or more predetermined work increments corresponding to operation of the motor, and communicating the one or more effort indicators to an operator.

B. A method that includes grasping a user input device in communication with a surgical tool of a robotic surgical system, the surgical tool having an end effector with opposing jaws, manipulating the user input device to actuate a motor that opens and closes the jaws, calculating with a computer system in communication with the surgical tool work completed by the motor, generating with the computer system one or more effort indicators indicative of the work completed by the motor, and communicating the one or more effort indicators to an operator.

Each of embodiments A and B may have one or more of the following additional elements in any combination: Element 1: wherein calculating the work completed by the motor comprises measuring torque assumed by the motor with a torque sensor, measuring a rotational angle of the motor with a rotary encoder, and calculating the work completed by the motor based on the torque and the rotational angle measured. Element 2: wherein the one or more effort indicators comprise auditory feedback and communicating the one or more effort indicators to the operator comprises generating a sound audible to the operator when the work completed by the motor meets or exceeds the one or more predetermined work increments. Element 3: further comprising increasing a pitch of the sound upon meeting or exceeding succeeding predetermined work increments of the one or more predetermined work increments. Element 4: wherein the one or more effort indicators comprise tactile feedback and communicating the one or more effort indicators to the operator comprises generating a vibration in the user input device. Element 5: further comprising increasing a magnitude or duration of the vibration upon meeting or exceeding succeeding predetermined work increments of the one or more predetermined work increments. Element 6: wherein the one or more effort indicators comprise visual feedback and communicating the one or more effort indicators to the operator comprises generating a graphic animation viewable by the operator.

Element 7: wherein the user input device is selected from the group consisting of a hand-held actuator module, a joystick, an exoskeletal glove, a master manipulator, and any combination thereof. Element 8: wherein manipulating the user input device to actuate the motor comprises generating a signal sent to the computer system by manipulating the user input device, and causing operation of the motor based on the signal and thereby driving a drive input of the surgical tool with the motor to open or close the jaws. Element 9: wherein calculating the work completed by the motor comprises measuring torque assumed by the motor with a torque sensor, measuring rotational angle of the motor with a rotary encoder, and calculating the work completed by the motor based on the torque and the rotational angle measured. Element 10: wherein generating the one or more effort indicators comprises setting one or more predetermined work increments corresponding to operation of the motor, and generating and communicating in real-time the one or more effort indicators when the work completed by the motor meets or exceeds the one or more predetermined work increments. Element 11: wherein the one or more predetermined work increments comprise work increments of a set magnitude. Element 12: wherein the one or more predetermined work increments comprise percent increments of total work possible for the motor to fully close the jaws. Element 13: wherein the one or more effort indicators comprise auditory feedback and communicating the one or more effort indicators to the operator comprises generating a sound audible to the operator. Element 14: further comprising increasing a pitch of the sound upon meeting or exceeding succeeding predetermined work increments of the one or more predetermined work increments. Element 15: wherein the one or more effort indicators comprise tactile feedback and communicating the one or more effort indicators to the operator comprises generating a vibration in the user input device. Element 16: further comprising increasing a magnitude or duration of the vibration upon meeting or exceeding succeeding predetermined work increments of the one or more predetermined work increments. Element 17: wherein the one or more effort indicators comprise visual feedback and communicating the one or more effort indicators to the operator comprises generating a graphic animation. Element 18: wherein the graphic animation comprises a meter rendered as on overlay on a visual display and graphically displaying a range of previous work values obtained for the end effector in conjunction with current work values.

By way of non-limiting example, exemplary combinations applicable to A and B include: Element 2 with Element 3; Element 4 with Element 5; Element 8 with Element 9; Element 11 with Element 12; Element 13 with Element 14; Element 15 with Element 16; and Element 17 with Element 18.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A method, comprising:
   grasping a user input device in communication with a surgical tool of a robotic surgical system, the surgical tool including an end effector with opposing jaws;
   squeezing the user input device and thereby actuating a motor that closes the jaws and clamps down on tissue at a surgical site;
   calculating with a computer system in communication with the surgical tool work completed by the motor to close the jaws and clamp down on the tissue;
   generating with the computer system one or more effort indicators when the work completed by the motor meets or exceeds one or more predetermined work increments corresponding to operation of the motor; and
   communicating the one or more effort indicators to an operator.

2. The method of claim 1, wherein calculating the work completed by the motor comprises:
   measuring torque assumed by the motor with a torque sensor;
   measuring a rotational angle of the motor with a rotary encoder; and
   calculating the work completed by the motor based on the torque and the rotational angle measured.

3. The method of claim 1, wherein the one or more effort indicators comprise auditory feedback and communicating the one or more effort indicators to the operator comprises generating a sound audible to the operator when the work completed by the motor meets or exceeds the one or more predetermined work increments.

4. The method of claim 3, further comprising increasing a pitch of the sound upon meeting or exceeding succeeding predetermined work increments of the one or more predetermined work increments.

5. The method of claim 1, wherein the one or more effort indicators comprise tactile feedback and communicating the one or more effort indicators to the operator comprises generating a vibration in the user input device.

6. The method of claim 5, further comprising increasing a magnitude or duration of the vibration upon meeting or exceeding succeeding predetermined work increments of the one or more predetermined work increments.

7. The method of claim 1, wherein the one or more effort indicators comprise visual feedback and communicating the one or more effort indicators to the operator comprises generating a graphic animation viewable by the operator.

8. A method, comprising:
   grasping a user input device in communication with a surgical tool of a robotic surgical system, the surgical tool having an end effector with opposing jaws;
   manipulating the user input device to actuate a motor that opens and closes the jaws;
   calculating with a computer system in communication with the surgical tool work completed by the motor;

generating with the computer system one or more effort indicators indicative of the work completed by the motor; and communicating the one or more effort indicators to an operator.

9. The method of claim 8, wherein the user input device is selected from the group consisting of a hand-held actuator module, a joystick, an exoskeletal glove, a master manipulator, and any combination thereof.

10. The method of claim 8, wherein manipulating the user input device to actuate the motor comprises:

generating a signal sent to the computer system by manipulating the user input device; and causing operation of the motor based on the signal and thereby driving a drive input of the surgical tool with the motor to open or close the jaws.

11. The method of claim 10, wherein calculating the work completed by the motor comprises:

measuring torque assumed by the motor with a torque sensor;

measuring rotational angle of the motor with a rotary encoder; and calculating the work completed by the motor based on the torque and the rotational angle measured.

12. The method of claim 8, wherein generating the one or more effort indicators comprises:

setting one or more predetermined work increments corresponding to operation of the motor; and generating and communicating in real-time the one or more effort indicators when the work completed by the motor meets or exceeds the one or more predetermined work increments.

13. The method of claim 12, wherein the one or more predetermined work increments comprise work increments of a set magnitude.

14. The method of claim 12, wherein the one or more predetermined work increments comprise percent increments of total work possible for the motor to fully close the jaws.

15. The method of claim 8, wherein the one or more effort indicators comprise auditory feedback and communicating the one or more effort indicators to the operator comprises generating a sound audible to the operator.

16. The method of claim 15, further comprising increasing a pitch of the sound upon meeting or exceeding succeeding predetermined work increments of the one or more predetermined work increments.

17. The method of claim 8, wherein the one or more effort indicators comprise tactile feedback and communicating the one or more effort indicators to the operator comprises generating a vibration in the user input device.

18. The method of claim 17, further comprising increasing a magnitude or duration of the vibration upon meeting or exceeding succeeding predetermined work increments of the one or more predetermined work increments.

19. The method of claim 8, wherein the one or more effort indicators comprise visual feedback and communicating the one or more effort indicators to the operator comprises generating a graphic animation.

20. The method of claim 19, wherein the graphic animation comprises a meter rendered as on overlay on a visual display and graphically displaying a range of previous work values obtained for the end effector in conjunction with current work values.

* * * * *